United States Patent
Damadian et al.

(10) Patent No.: US 7,343,191 B1
(45) Date of Patent: Mar. 11, 2008

(54) MRI SYSTEM

(75) Inventors: Raymond V. Damadian, Woodbury, NY (US); John D. Kersten, Port Jefferson Station, NY (US)

(73) Assignee: Fonar Corporation, Melville, NY (US)

( * ) Notice: Subject to any disclaimer, the term of this patent is extended or adjusted under 35 U.S.C. 154(b) by 754 days.

(21) Appl. No.: 10/033,116

(22) Filed: Dec. 27, 2001

(51) Int. Cl.
*A61B 5/05* (2006.01)

(52) U.S. Cl. .................. 600/410; 324/318; 324/322

(58) Field of Classification Search .............. 600/411, 600/410, 418; 324/18, 322, 318
See application file for complete search history.

(56) References Cited

U.S. PATENT DOCUMENTS

| | | | |
|---|---|---|---|
| 2,480,178 A | 8/1949 | Zinberg | |
| 3,360,640 A | 12/1967 | Ernst-Otto Seitz et al. | |
| 3,437,803 A | 4/1969 | Ernst-Otto Seitz et al. | |
| 4,060,724 A | 11/1977 | Heine et al. | |
| 4,605,990 A | 8/1986 | Wilder et al. | |
| 4,613,926 A | 9/1986 | Heitman et al. | |
| 4,763,984 A | 8/1988 | Awai et al. | |
| 4,825,341 A | 4/1989 | Awai | |
| 4,922,385 A | 5/1990 | Awai | |
| 4,966,450 A | 10/1990 | Mori | |
| 5,016,152 A | 5/1991 | Awai et al. | |
| 5,345,531 A | 9/1994 | Keplinger et al. | |
| 5,353,786 A | 10/1994 | Wilk | |
| 5,406,641 A | 4/1995 | Bigley, Jr. et al. | |
| 5,416,875 A | 5/1995 | Keplinger et al. | |
| 5,479,322 A | 12/1995 | Kacheria | |
| 5,485,541 A | 1/1996 | Bigley, Jr. et al. | |
| 5,530,940 A | 6/1996 | Ludwig, Jr. et al. | |
| 5,616,638 A | 4/1997 | Hallden-Abberton et al. | |
| 5,627,470 A * | 5/1997 | Kuth ......................... 324/318 |
| 5,708,749 A | 1/1998 | Kacheria | |
| 5,779,353 A | 7/1998 | Kacheria | |
| 5,816,128 A | 10/1998 | Bigley, Jr. et al. | |
| 5,901,449 A | 5/1999 | Ulbrich et al. | |
| 5,916,648 A | 6/1999 | Daecher | |
| 5,930,442 A | 7/1999 | Ambramowicz et al. | |
| 6,091,878 A | 7/2000 | Ambramowicz et al. | |
| 6,207,747 B1 | 3/2001 | Ilenda et al. | |
| 6,208,145 B1 * | 3/2001 | Danby et al. ............... 324/319 |
| 6,215,947 B1 | 4/2001 | Ambramowicz et al. | |
| 6,219,480 B1 | 4/2001 | Cassarly et al. | |

(Continued)

OTHER PUBLICATIONS

"Fiberstars Announces New Energy Efficient Lighting System", Fiberstars, Inc., http://www.fiberstars.com, pp. 1-3, Apr. 11, 2001.

(Continued)

*Primary Examiner*—Brian L. Casler
*Assistant Examiner*—John F. Ramirez
(74) *Attorney, Agent, or Firm*—Brandon N. Sklar; Kaye Scholer LLP

(57) ABSTRACT

In one example, an illumination system is provided in an MRI system including an open MRI assembly comprising a pole covered by a canopy. The MRI system is within a shielded room. A light source is provided outside of the shielded room, at least one light projector is connected to the canopy, and optical fibers couple the light source to the light projector. The light projector is preferably flexible. The light projector or projectors increase the illumination in the imaging volume, facilitating medical procedures conducted on a subject within the imaging volume.

50 Claims, 5 Drawing Sheets

U.S. PATENT DOCUMENTS

| | | | |
|---|---|---|---|
| 6,294,915 B1 * | 9/2001 | Murphy et al. | 324/318 |
| 6,382,824 B1 | 5/2002 | Prasad et al. | |
| 6,541,973 B1 * | 4/2003 | Danby et al. | 324/318 |
| 6,617,852 B1 * | 9/2003 | Danby et al. | 324/318 |
| 6,697,664 B2 * | 2/2004 | Kienzle, III et al. | 600/427 |
| 6,879,157 B1 * | 4/2005 | Bonanni et al. | 324/309 |
| 2002/0057088 A1 * | 5/2002 | Carrozzi et al. | 324/318 |
| 2004/0249261 A1 * | 12/2004 | Torchia et al. | 600/411 |

OTHER PUBLICATIONS

"Micro Illumination Products, Cogent Technologies", http://www.cogentlight.com/illprod2.html, p. 1, 2001.

"Putting Surgery in a New Light", Cogent Technologies, http://www.cogentlight.com/illtech2c.html, pp. 1-2, 2001.

"Micro Illumination Products", Cogent Technologies, http://www.cogentlight.com/illprod2b.html, p. 1, 2001.

*Press Releases*, "Cogent Light Fact Sheet", Cogent Technologies, http://www.cogentlight.com/facts.html, pp. 1-2, 2001.

*Press Release*, "Putting Surgery Via New Light", Cogent Technologies, http://www.cogentlight.com/illtech2d.html, p. 1, 2001.

"How to Choose Surgical Lights", Outpatient Surgery Magazine, pp. 1-4, May 2000.

"601 Illuminator—Specification and Submittal Sheet", Fiberstars, 44259 Nobel Drive, Fremont, CA 94538, pp. 1-2, 1999.

"Fiberstars Lighting for the 21st Century—Specification and Submittal Sheet 210, 219, 220", Fiberstars, 44259 Nobel Drive, Fremont, CA 94538, pp. 1-2, 1997.

"Fiberscape Fiber Twist Fixture—FS 210 Installation Instructions", Fiberstars, 2883 Bayview Drive, Fremont, CA 94538, pp. 1-2, Jul. 31, 1995.

"Optical Port Kit—#A10980 Installation Instructions", Fiberstars, 44259 Nobel Drive, Fremont, CA 94538, pp. 1 (Undated).

\* cited by examiner

MRI SYSTEM

FIELD OF THE INVENTION

The present invention relates to magnetic resonance imaging systems including a lighting system.

BACKGROUND OF THE INVENTION

Magnetic resonance imaging ("MR") is a well known, highly useful technique for diagnosing abnormalities in biological tissue. MRI can detect abnormalities that are difficult or impossible to detect by other techniques, without the use of x-rays or invasive procedures.

MRI can be of great assistance during medical procedures. For example, MRI has been used for pre-operative and postoperative imaging to identify and assess the condition of tissue of interest. MRI has also been used during fine-needle aspiration cytology to help the doctor guide the needle to the site of interest, such as a tumor. See, for example, U.S. Pat. No. 6,208,145 B1, assigned to the assignee of the present invention and incorporated by reference, herein. MRI has also been used in stereotactic neurosurgery. The advance of other instruments, such as a catheter or an endoscope, can also be followed and guided to a site of interest by MRI. See, for example, U.S. Pat. No. 6,249,695 B1 and U.S. Pat. No. 5,647,361, which are both assigned to the assignee of the present invention and incorporated by reference, herein. The catheter can be used in the treatment of the tissue of interest, such as a tumor, by delivering medication, isotopes or other such treatments, for example. The effect of the treatment on the tissue may also be monitored by MRI, as the treatment is being conducted. See for example, U.S. Pat. No. 6,208,145 B1 and U.S. Pat. No. 6,280,383 B1, both assigned to the assignee of the present invention and incorporated by reference herein.

MRI systems are available with imaging volumes large enough to conduct surgery and other medical procedures. For example, in U.S. Pat. No. 6,208,145 B1, assigned to the assignee of the present invention and incorporated by reference herein, an open MRI assembly is disclosed wherein a physician or other medical personnel may conduct activities within the frame of the assembly, adjacent to the patient.

The magnet assembly of the MRI system may define a room for conducting a medical procedure and may be large enough to contain an entire surgical team. See, for example, U.S. Pat. No. 6,201,394 B1, assigned to the assignee of the present invention and incorporated by reference herein. The Quad™ 7000 and Quad™ 12000 Open MRI Systems, available from FONAR Corporation, Melville, N.Y., are also suitable for performing surgery and other medical procedures.

Rooms for conducting medical procedures, particularly rooms for conducting surgery, typically use large overhead lights for illumination. The lights are often fluorescent. The position and/or direction of the lights are usually adjustable so that the surgeon or other personnel can direct the light onto the site of interest. Typical medical lighting cannot be placed into the imaging volume of an MRI system, however, because fluorescent lighting may interfere with the magnetic field generated by the MRI System. In addition, in an Open MRI System, the upper pole can cast a shadow within the imaging volume.

An improved lighting system is needed to facilitate the performance of medical procedures in an imaging volume of an MRI system.

SUMMARY OF THE INVENTION

In accordance with one embodiment of the invention, a magnetic resonance imaging (MRI) system is disclosed comprising a magnet assembly defining an imaging volume. A shielded room surrounds the magnet assembly. A light source is provided outside of the shielded room. At least one light projector is provided within the room to direct illumination within the imaging volume. Means are provided for optically connecting the light source to the at least one light projector. The means, which are preferably optical fibers and more preferably optical fibers in the form of a bundle, extend through a wall of the shielded room, to the light projector.

The light projector is preferably flexible. The light projector may comprise a plurality of segments and at least one of the segments is movable with respect to an adjacent segment. Each movable segment may comprise a first, rounded end and a second, recessed end for receiving the rounded end of an adjacent segment. The rounded end of one segment moves within the recessed end of the adjacent segment.

The MRI system preferably comprises a magnet assembly comprising a ferromagnetic frame supporting opposing ferromagnetic poles. Canopies are provided over each pole. One or more light projectors are preferably connected to a canopy over one of the poles. The canopy preferably has at least one recessed portion and the at least one light projector is connected to the first canopy within the recessed portion. The poles may be aligned vertically and in that case, the light projectors are preferably connected to the canopy over the upper pole.

In accordance with another embodiment of the invention, an MRI system comprises a ferromagnetic frame and first and second opposing ferromagnetic poles supported by the ferromagnetic frame. A first canopy covers the first pole and a second canopy covers the second pole. An imaging volume is defined between the canopies. A light projector is connected to the first canopy.

In accordance with another embodiment of the invention, an open MRI system is disclosed comprising a magnet assembly comprising a ferromagnetic frame and first and second opposing ferromagnetic poles supported by the ferromagnetic frame. A first canopy is provided over the first pole and a second canopy is provided over the second pole. An imaging volume is defined between the first and second canopies. The MRI system further comprises a shielded room comprising at least one wall. The magnet assembly is within the room. A light source is provided outside of the shielded room and a plurality of optical fibers convey light from the light source through a wall of the shielded room into the shielded room. A light projector is connected to the first canopy at a first location. The optical fibers enter the first canopy at a second location and exit the first canopy through the first location, into the at least one light projector. Preferably, a plurality of light projectors are provided, the light projectors are connected to the first canopy within recesses in the cavity and the light projector is flexible.

In accordance with another embodiment of the invention, a method of conducting a medical procedure is disclosed comprising positioning a subject in an imaging volume of an MRI magnet assembly, conducting a medical procedure on the subject, conducting magnetic resonance imaging of the subject and illuminating the subject with a light projector connected to the MRI magnet assembly.

DESCRIPTION OF THE PREFERRED EMBODIMENTS

Figure 1:
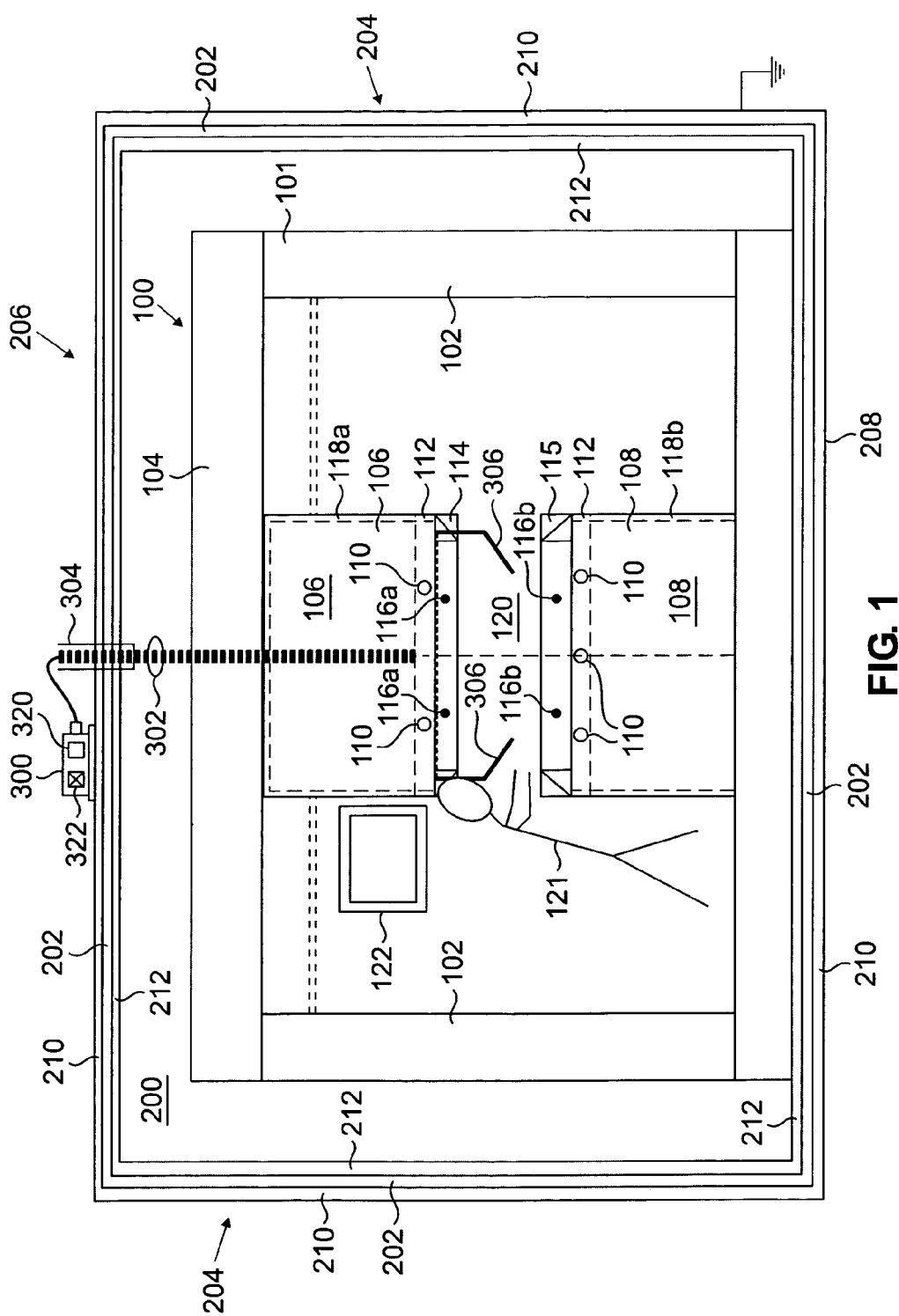
FIG. 1 is a side view of an Open MRI System showing an illumination system in accordance with one embodiment of the invention.

FIG. 1 is a side view of an Open MRI System 100 in accordance with one embodiment of the present invention. The MRI system 100 comprises an MRI magnet assembly 101 comprising a ferromagnetic frame. The frame comprises ferromagnetic elements 102 connected at their ends to ferromagnetic pole supports 104. The pole supports 104 support ferromagnetic poles 106, 108 with opposing pole faces. The ferromagnetic supporting elements may be opposing ferromagnetic plates, as described in U.S. Pat. No. 6,201,394 B1, or four ferromagnetic posts, as described in U.S. Pat. No. 6,201,394 B1, U.S. Pat. No. 6,075,364 and U.S. Pat. No. 5,754,085, which are assigned to the assignee of the present invention and are incorporated by reference herein, in their entireties. Shim coils (not shown) for adjusting the magnetic field are also provided, as is known in the art. Gradient field generating coils 110 are provided in a plate 112 adjacent to each of the poles 106, 108. Upper and lower transmitter coil plates 114, 115 are typically provided for supporting upper and lower portions 116a, 116b of a rectangular transmitter coil, respectively. A transmitter coil spacer plate (not shown) is typically provided between each transmitter coil plate 114, 115 and the gradient coil plates 112. Portions of the transmitter coil 116a, 116b within each plate 114, 115, respectively lie in a plane parallel to the pole faces. The transmitter coil plate 114 and the gradient coil plate 112 are typically made of a flame retardant, insulative material, such as polyvinylchloride ("PVC"). Other types of transmitter coils may be used, as well.

Figure 2:
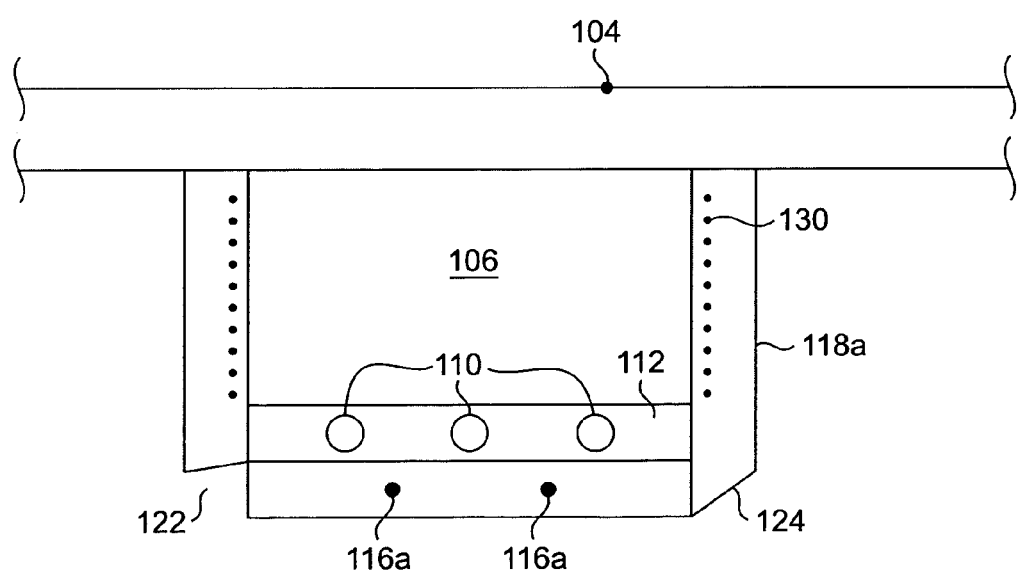
FIG. 2 is a cross-sectional view of an upper pole and accompanying accessories of the Open MRI System of FIG. 1.

FIG. 2 is a cross-sectional view of the upper pole 106 and accompanying accessories (gradient field generating coils 110, plate 112, transmitting coil 116a and plate 114). Canopies 118a, 118b of PVC, for example, are typically provided over the poles 106, 108 (and accessories), respectively. The canopy is typically about ⅛ inch to about ¼ inch thick. Also shown in cross-section in FIG. 2 are the windings of an electromagnetic coil 130 around the pole 106. The coil 130 generates a magnetic field through the pole 106 when driven by an alternating current. A coil is provided around the lower pole 108, as well.

Returning to FIG. 1, the space between the canopies over the upper and lower poles 106, 108 define an imaging volume 120 for receiving of a subject (not shown) for an MRI procedure.

As discussed above, the magnet assembly 101 is large enough for medical personnel, such as a doctor 121, to access the imaging volume 120 and a patient (not shown) within the imaging volume. A medical procedure may therefore be conducted within the magnet assembly 101. The magnet assembly 101 may be large enough to define a room for conducting the medical procedure, as described in U.S. Pat. No. 6,225,805 B1, which is assigned to the assignee of the present invention and is incorporated by reference herein.

Preferably, two recessed portions 122, 124 are provided on opposite sides of the bottom of the canopy 118, as shown in FIG. 2. The recessed portions 122, 124 provide additional room for a doctor or other such personnel in the room to lean into the imaging volume 120 during a medical procedure, as shown in FIG. 1. The recessed portions 122, 124 may be symmetrically arranged around the periphery of the canopy 118, as shown in the bottom view of FIG. 4, or asymmetrically arranged. One recessed portion or more than two recessed portions may be provided.

The magnet assembly 101 is typically situated in a shielded room 200, to block interference from external radio frequency sources, as is known in the art. The shielded room 200 may comprise walls 202 of particle board, for example, forming the side walls 204, ceiling 206 and floor 208 of the room 200. Particle board is a resin based product comprising wood chips and saw dust. Steel sheets 210, 212 are provided on opposite sides of each wall 202, forming the shield. 25 gauge steel may be used, for example. The walls are typically about ¹³⁄₁₆ inches thick. The shield is referred to as a Faraday shield. Any doors and windows in the room are preferably shielded through use of a conductive mesh. Conductive films may also be provided on the windows. The mesh and film, if present, are preferably electrically connected to the shielding of the room, which is grounded. Any equipment in the room is preferably adapted for low radio frequency emission, as is also known in the art. For example, a projectors (not shown) may be provided to project the MR images onto a screen 122 on a wall of the room, for use by the medical personnel in the room during a medical procedure. The projectors may be surrounded by a shield. Alternatively a shielded video monitor may be provided. Fixtures, such as overhead lights (not shown), may be similarly shielded. Such shielding for equipment in the room is also known in the art.

A patient bed (not shown) is provided over the canopy of the bottom pole 108. The bed may be a typical bed used in MRI procedures. Preferably, the bed can move into and out of the imaging volume, can rotate in either direction about a polar axis through the poles of the MRI assembly, can move along a plane perpendicular to the polar axis and can tilt about a longitudinal axis of the bed. Thus, it can be disposed in any radial direction with any part of the patient's body in the imaging volume 120. A suitable bed is described in U.S. Pat. No. 6,208,145, for example, assigned to the assignee of the present invention and incorporated by reference, herein.

In accordance with the present invention, the Open MRI System 100 further comprises a lighting system comprising a light projector 306. In the preferred embodiment, a plurality of light projectors 306 are connected to the canopy 118a of the upper pole 106, within the recessed portions 122, 124. Four light projectors 306 are preferred.

In this embodiment, a light source 300 is provided to supply light to the light projector 306. The light source 300 is preferably an alternating current ("AC") light source, which is generally less expensive than a DC light source and is easier to replace. The light source 300 preferably comprises a metal halide bulb 320 with a power of from about 150 to about 200 watts. In this power range, the metal halide bulb 320 emits light in a temperature range of about 4000-4400° Kelvin, which is close to natural daylight. Daylight is preferred for surgical procedures. A fan 322 cools the bulb. The bulb 320 and the fan 322 are shown schematically in FIG. 1.

The light source 300 is preferably located outside of the shielded room 200 because the motor driving the fan 322 can interfere with the operation of the MRI System 100. In addition, the light source 300 can generate a significant amount of heat that can cause discomfort to the patient and medical personnel in the room 200.

Optical fibers 302 are connected to the light source 300 and a wave guide 304 extends through the shielded room 200. The optical fibers 302 enter the interior of the shielded room 200 through the wave guide 304. The wave guide 304 may be a brass sleeve, for example. The sleeve 304 can have an inner diameter of about 2 inches and a length of about 8 inches, for example, to ensure that essentially no electromagnetic radiation can enter or exit the room through the sleeve.

The optical fibers 302 enter one or more of the light projectors 306, which in this embodiment support the optical fibers and aim the light carried by the fibers to a site of interest within the imaging volume 120.

The optical fibers 302 are preferably in the form of four bundles 302a, 302b, 302c, 302d of glass or plastic optical fibers. For example, 75 optical fibers may be bundled within a sheath. Such a bundle may have a diameter of about ⅜ inch, for example. A separate bundle may be provided for each light projector 306. Each bundle may be connected to the same or multiple ports of the light source 300. Alternatively, a quartz fiber could be used instead of a bundle of glass or plastic optical fibers.

Figure 3:
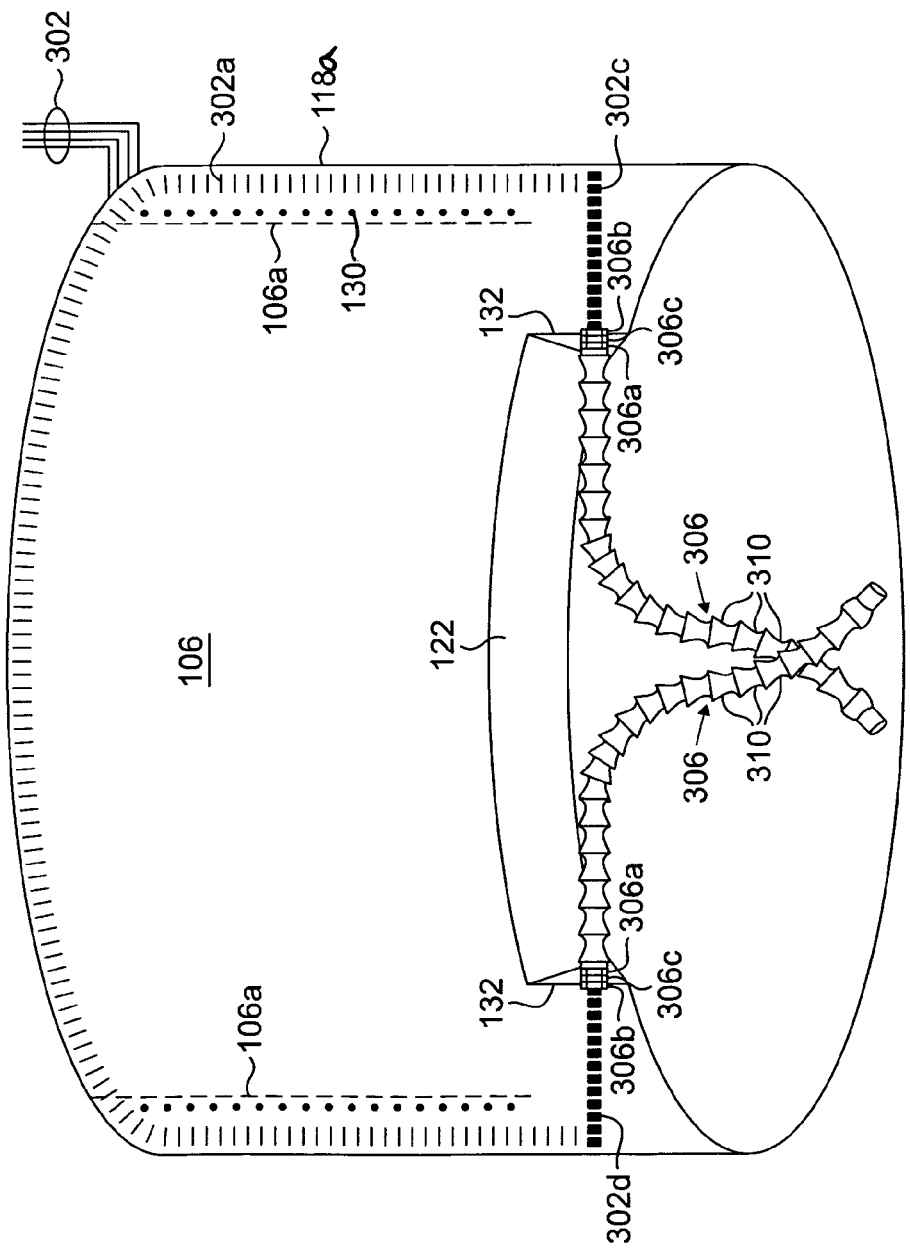
FIG. 3 is a perspective view of the upper pole of FIG. 2, showing optical fibers and light projectors supporting the optical fibers within an imaging volume of the system of FIG. 1.

Preferably, the four fiber optic bundles, 302a, 302b, 302c, 302d extend between the canopy 118a and the upper pole 106, down the length of the pole and plates, as shown in FIG. 3. The four fiber optic bundles 302 preferably split into first and second groups of bundles 302a, 302b at the top of the upper pole 106. In this example there are two bundles in each group. One group 302a continues down the pole while the other group 302b extends around the periphery of the pole 106 to the opposite side of the pole. The second group 302b then extends down the length of the pole 106, as well. The first and second groups 302a, 302b then split into first and second bundles 302c, 302d and third and fourth bundles, 302e, 302f, respectively. Alternatively, passages may be formed in the wall of the canopy 118a to carry the bundles of optical fibers partially or completely to the light projectors 306, as long as the diameter of each bundle is sufficiently smaller than the thickness of the canopy wall. Such passages may be formed by drilling or may be formed during molding of the canopy. The outer boundary 106a of the pole 106 is indicated for clarity.

Figure 4:
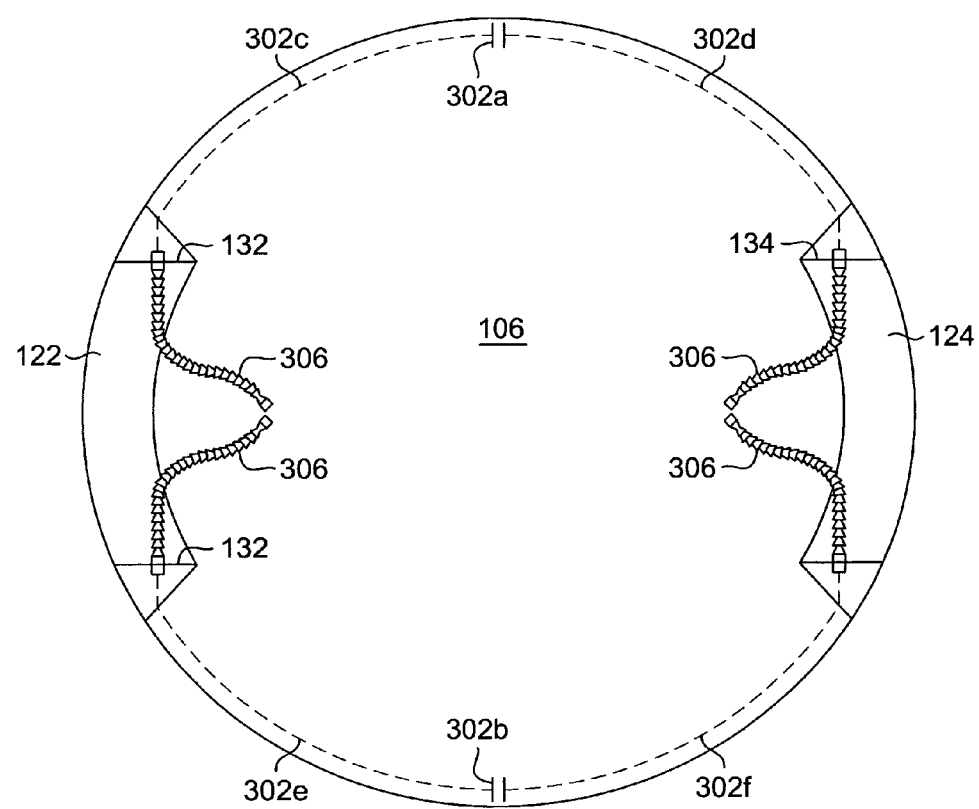
FIG. 4 is a bottom view of the upper pole of FIG. 3.

Each one of the third, fourth, fifth and sixth bundles 302c-302f extend through a respective opening in the canopy 118a and enter a respective light projector 306. FIG. 4 is a bottom view of the upper pole 106, showing the light projectors 306. The recessed portions 122, 124 include side walls 132 and the light projectors 306 are preferably connected to the side walls.

While four light projectors 306 are preferred, more or fewer light projectors may be provided. It is noted that it is not desirable to provide too much illumination in the imaging volume 120 because too much illumination may obscure the true nature of the tissue. For example, if the light is too bright, it may be difficult to identify the pink color of tissue resulting from a return of blood flow, or the blue color of tissue deprived of blood flow and/or oxygen, during a medical procedure.

FIG. 3 shows the connection between the light projectors 306 and the side walls 132 of a recessed portion 122 of the canopy 118a. Openings for passage of the fiber optic bundles may be formed by drilling holes through the canopy 118a. In this embodiment, the end of each light projector 306 comprises a threaded hollow sleeve 306a. Two nuts 306b, 306c are provided on the sleeve 306a. To attach the light projectors 306 to the canopy 118a, a hole is provided through the side wall 132. The nut 306b is removed and the sleeve 306a is inserted through the hole. The nut 306b is screwed onto the sleeve 306a so that each nut 306b, 306c is on an opposite side of the side wall 132. The nuts 306b, 306c are tightened against both sides of the side wall 132 to secure the light projector 306 in place. After a light projector 306 is connected to a side wall 132, the fiber optic bundle is inserted into the hollow sleeve, to the end of the light projector 306.

Figure 5:
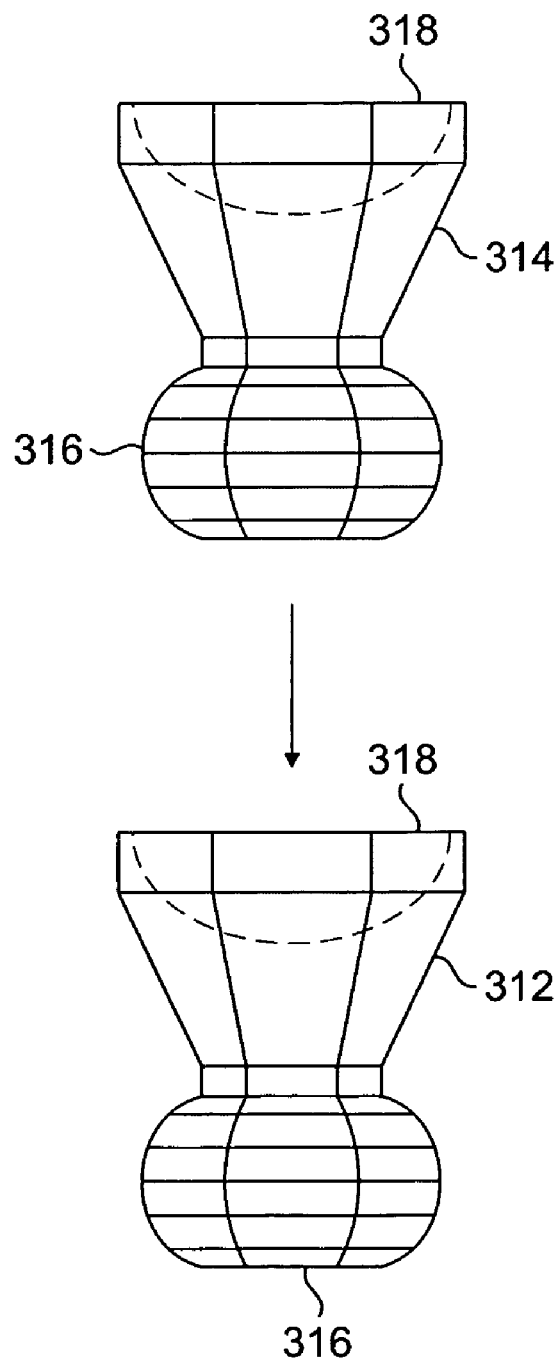
FIG. 5 is a side view of two segments of the light projector in accordance with one embodiment of the invention.

Preferably, the light projectors 306 are flexible. In this embodiment, the light projectors 306 comprise a plurality of segments 310. FIG. 5 shows two adjacent segments 312, 314, separated for illustrative purposes. Each segment has a first, rounded end 316 and a second, recessed end 318 to receive the rounded end 316 of an adjacent segment in a snap fit. The recess has a radius "r" slightly larger than the radius "R" of the rounded end 316 of the adjacent segment. The inner diameter "d" of the edge of the recess is slightly smaller than the widest diameter "D" of the rounded end 316. When connected, the rounded end 316 is rotatable within the recessed end 318, enabling flexing of the light projector 306. Light can thereby be directed onto a desired location by medical personnel during a medical procedure. Each segment 310 is hollow and the rounded end 316 and the recessed end 318 include openings for passage of the fiber optic bundle. The necessary number of segments 310 may be connected to provide a light projector 306 of the desired length. While it is preferred that the entire light projector 306 be flexible by providing segments 310 that move with respect to each other along the entire length of the light projector 306, that is not required. Only two or several adjacent segments may be movable for limited flexibility.

Optics may be provided at the end of the light projector 306 to increase the focus or the dispersal of the emitted light. The material of the light projectors 306 is preferably non-metallic. Preferably, the material of the light projector 306 is water proof. A plastic material may be used, for example. The light projectors 306 may a FiberScape™ Fiber Twist™ Fixture available from FIBERSTARS®, Fremont Calif., for example, which are made of Lexan®, a black plastic composite material.

An example of a light source 300 is a 405 Illuminator with a 150 or 200 watt metal halide bulb or a 601 Illuminator with a 200 watt metal halide bulb, both available from FIBERSTARS®, Fremont, Calif. The 405 or 601 Illuminators can be driven by a 120 voltage power supply. Both units include a fan to cool the bulb. Four fiber optic bundles 302a, 302b, 302c, 302d, as described above, may be connected to a single optical port of the 405 or 601 Illuminators. The fiber optic bundles 302 are mounted on the side of the 405 and 601 Illuminators, as shown in FIG. 1. It is therefore preferred that the 405 or 601 Illuminator be mounted horizontally on the top of the ceiling 206 of the shielded room 200, as shown, to avoid over heating of the optical fibers.

During an MRI guided medical procedure, such as a surgical procedure, when it is necessary to illuminate a portion of the patient to a greater degree than the illumination already present in the imaging volume 120, one or several of the light projectors 306 may be directed toward that portion. When the additional illumination is not needed, the light projectors 306 may be folded upward, out of the way. The level of diffuse light in the imaging volume 120 may be increased by aiming the light projectors 306 toward the flat bottom surface of the canopy. Since the light source 300 is outside of the MRI room 200 and no heat is generated by the optical fiber bundles in the light projectors 306, the light source 300 may be left on during the entire medical procedure, even when additional illumination is not needed. When illumination is needed, the illuminators may be folded back towards the patient and the site of interest.

Medical procedures that may be facilitated by being conducted within the imaging volume of an MRI system with improved illumination as described above include, without limitation, minimally and non-minimally invasive procedures such as biopsies, laproscopy, procedures using catheters or endoscopes and treatment regimens, such as injecting an isotope or other treatment into a tumor, for example.

While it is preferred that the light source 300 be outside of the room 200, it is not required. For example, if a fan is not required to cool the light source, the light source 300 may be within the shielded room 200.

In addition, while it is preferred that the light projectors 306 be connected to the canopy 118a over the upper pole 106, some or all of the light projectors 306 may be connected to the canopy 118b over the lower pole 108, as well. One or more of the light projectors 306 may also be supported by a stand placed adjacent to the imaging volume 120, instead of or along with connecting the light projectors 306 to a canopy 118a, 118b.

The MRI system 100 of FIG. 1 is an example of an MRI system that may be used in the present invention. The illumination system of the present invention may be used with other types of MRI systems known in the art to conduct medical procedures, as well. For example, the MRI system may comprise an upright magnet assembly for imaging a patient in a standing position, as disclosed in U.S. Pat. No. 6,075,364, assigned to the assignee of the present invention and incorporated by reference herein, for example. Such an MRI assembly may also be situated within the shielded MRI room 200. In an upright magnet assembly, the poles of the magnet assembly create a magnetic field extending across the imaging volume in a horizontal orientation, instead of a vertical orientation, as in the magnet assembly 100 of FIG. 1. The patient is situated within the imaging volume between the poles (and accessories, if any). The poles are covered by respective canopies and the light projectors 306 may be connected to one or both of the canopies, as described above. The light projectors 306 may be supported by a stand near the imaging volume, as well.

The magnet assembly may also comprise a C-shaped ferromagnetic frame, as is known in the art. C-shaped ferromagnetic magnet assemblies are also described in U.S. Pat. No. 6,075,364, which is assigned to the assignee of the present invention and is incorporated by reference, herein. Canopies may be provided over opposing poles supported by the C-shaped frame and the light projectors 306 may be connected to one or both canopies, as described above. Lighting may be provided in the other manners described above, as well.

The ferromagnetic frame may also comprise a cylindrical side wall connected to opposing circular pole supports, as is also described in U.S. Pat. No. 6,201,394 B1, which is also assigned to the assignee of the present invention and is incorporated by reference, herein.

The lighting system of the present invention may be readily retrofit onto existing MRI systems, as would be apparent to one of ordinary skill in the art.

While in the preferred embodiment, the light projector is a fixture optically coupled to a light source by optical fibers, the light projector 306 may also contain a light source.

While a transmitting coil, such as the transmitting coil 116a, 116b, is typically provided in upper and lower transmitter plates 114, 115, the transmitting coil may be provided in the imaging volume 120 proximate the subject of the MRI procedure. In that case, the upper and lower transmitter plates would not be necessary. Canopies 118a, 118b would still be provided over the poles and other accessories and the illumination system may still be mounted, as described above.

One of skill in the art will understand that other modifications may be made to the embodiments described above without going beyond the scope of the present invention, which is defined by the following claims.

We claim:

1. A magnetic resonance imaging (MRI) system, comprising:
   a magnet assembly defining an imaging volume and at least one recessed portion;
   a shielded room surrounding the magnet assembly;
   a light source outside of the shielded room;
   at least one light projector within the room to direct illumination within the imaging volume, the light projector being bendable along a length;
   the at least one light projector being coupled to the at least one recessed portion of the magnet assembly; and
   means for optically connecting the light source to the at least one light projector, said means extending through a wall of the shielded room.

2. The MRI system of claim 1, wherein said means comprises a plurality of optical fibers.

3. The MRI system of claim 2, wherein the plurality of optical fibers extend through the at least one light projector, and the at least one light projector supports the optical fibers.

4. The MRI system of claim 2, comprising a plurality of optical fibers in the form of at least one bundle.

5. The MRI system of claim 1, further comprising a wave guide extending through the wall, wherein said means extends through the wave guide.

6. The MRI system of claim 1, wherein the at least one light projector comprises a plurality of segments, and at least one segment is movable with respect to an adjacent segment.

7. The MRI system of claim 6, wherein each movable segment comprises a first, rounded end and a second, recessed end for receiving the rounded end of an adjacent segment, wherein the rounded end of one segment can move within the recessed end of the adjacent segment.

8. The MRI system of claim 1, wherein the at least one light projector is connected to the MRI assembly.

9. The MRI system of claim 8, wherein the at least one light projector is connected to the MRI assembly within the imaging volume.

10. The MRI system of claim 1, wherein the magnet assembly comprises:
    a ferromagnetic frame; and
    first and second opposing poles supported by the ferromagnetic frame, wherein the at least one light projector is coupled to one of the poles.

11. The MRI system of claim 10, wherein:
    the magnet assembly further comprises a first canopy over the first pole, the first canopy defining the at least one recessed portion; and the at least one light projector is connected to the first canopy within the at least one recessed portion.

12. The MRI system claim 11, wherein the means extends between the pole and the canopy to the at least one light projector.

13. The MRI system of claim 11, wherein the opposing poles are aligned along a vertical axis such that one of the poles is an upper pole and the other of the poles is a lower pole, wherein the at least one light projector is coupled to the upper pole.

14. The MRI system of claim 1, wherein the MRI system is an open MRI system.

15. The MRI system of claim 1, wherein the light source is an alternating current light source.

16. An open magnetic resonance imaging (MRI) system comprising:
    a magnet assembly comprising:
    a ferromagnetic frame;
    first and second opposing ferromagnetic poles supported by the ferromagnetic frame; and
    a first canopy over the first pole and a second canopy over the second pole, the first and second canopies defining an imaging volume therebetween;
    the system further comprising:
    a shielded room comprising at least one wall, wherein the magnet assembly is within the room;
    a light source outside of the shielded room;
    a plurality of optical fibers conveying light from the light source through a wall of the shielded room into the shielded room; and
    a light projector connected to the first canopy at a first location;
    wherein the optical fibers extend through the first canopy at a second location and out of the first canopy through the first location, into the light projector.

17. The open MRI system of claim 16, wherein the optical fibers extend from the first location to the second location, between the canopy and the first pole.

18. The open MRI system of claim 16, wherein the light projector is flexible.

19. The open MRI system of claim 18, wherein the light projector comprises a plurality of segments and at least one segment is movable with respect to an adjacent segment.

20. The open MRI system of claim 19, wherein each movable segment comprises a first, rounded end and a second, recessed end for receiving the rounded end of an adjacent segment, wherein the rounded end of one segment can move within the recessed end of the adjacent segment.

21. The open MRI system of claim 16, wherein the light source is an alternating current light source.

22. The open MRI system of claim 16, wherein the opposing poles are aligned along a vertical axis such that one of the poles is an upper pole and the other of the poles is a lower pole, and the light projector is connected to the first canopy.

23. The open MRI system of claim 16, wherein the first canopy has at least one recessed portion and the light projector is connected to the first canopy within the recessed portion.

24. The open MRI system of claim 23, wherein the first canopy has two recessed portions and the system comprises at least one light projector connected to the first canopy within each recessed portion, at respective locations, each light projector supporting a plurality of optical fibers extending out of the first canopy and into each light projector at the respective locations.

25. The open MRI System of claim 16, comprising a plurality of light projectors connected to the first canopy, each light projector supporting a plurality of optical fibers extending out of the first canopy and into each light projector at a respective location.

26. The MRI system of claim 16, wherein at least a portion of the optical fibers extend out of the first canopy substantially parallel to the first pole face.

27. A magnetic resonance imaging (MRI) system comprising:
    a ferromagnetic frame;
    first and second opposing ferromagnetic poles supported by the ferromagnetic frame, the first and second opposing poles having respective first and second opposing pole faces;
    a first canopy covering the first pole and a second canopy covering the second pole, the first and second canopies defining an imaging volume therebetween; and
    a light projector;
    wherein the first canopy has a recessed portion; and
    the light projector is connected to the first canopy within the recessed portion.

28. The MRI system of claim 27, further comprising a light source optically coupled to the light projector.

29. The MRI system of claim 28, further comprising optical fibers optically coupling the light source to the light projector.

30. The MRI system of claim 29, wherein the optical fibers are in the form of at least one bundle.

31. The MRI system of claim 29, wherein the light projector supports a portion of the optical fibers.

32. The MRI system of claim 29, wherein the light projector is connected to the first canopy at a first location, the optical fibers enter the canopy at a second location and the optical fibers extend from the first location to the second location, to enter the light projector.

33. The MRI system of claim 32, comprising a plurality of light projectors, at least one of the light projectors being connected to the canopy at a plurality of first locations within the recess, wherein the optical fibers split within the canopy and exit the canopy to enter each light projector at each respective first location.

34. The MRI system of claim 32, wherein the optical fibers extend from the first location to the second location between the first canopy and the first pole.

35. The MRI system of claim 27, further comprising:
    at least one second recessed portion;
    a plurality of light projectors, wherein at least one of the light projectors is connected to the first canopy within the first recessed portion; and
    at least one light projector is connected to the first canopy within the at least one second recessed portion.

36. The MRI system of claim 27, comprising a plurality of light projectors connected to the recessed portion.

37. The MRI system of claim 27, wherein the light projector is flexible.

38. The MRI system of claim 27, wherein the light sources comprises:
    a bulb to emit visible light; and
    a fan proximate the bulb to cool the bulb.

39. The MRI system of claim 27, wherein:
    the first canopy has a periphery; and
    the recessed portion is at the periphery.

40. The MRI System of claim 27, wherein the light projector comprises:
    a first end connected to the canopy within the recessed portion; and a second end to allow light to exit the light projector, during operation.

41. The MRI System of claim 40, wherein the light projector is bendable between the first and second ends.

42. The MRI system of claim 41, wherein the light projector comprises a plurality of segments, and at least one segment is movable with respect to an adjacent segment, to bend the light projector.

43. The MRI system of claim 42, wherein each movable segment comprises a first, rounded end and a second, recessed end for receiving the rounded end of an adjacent segment, and the rounded end of one segment can move within the recessed end of the adjacent segment, to bend the light projector.

44. A method of conducting a medical procedure comprising:
    positioning a subject in an imaging volume of a magnetic resonance imaging (MRI) magnet assembly;
    conducting a medical procedure on the subject;
    conducting magnetic resonance imaging of the subject; and
    flexing a light projector connected to the MRI magnet assembly in a recessed portion of the assembly to illuminate at least a selected portion of the subject.

45. The method of claim 44, comprising illuminating the subject with a light projector connected to a canopy covering a pole of the magnetic resonance imaging system.

46. The method of claim 44, wherein the MRI magnet assembly is within a shielded room, the method comprising:
    illuminating the subject with a light projector optically coupled to a light source outside of the shielded room.

47. The method of claim 46, further comprising conveying light from the light source to the light projector, through the canopy.

48. The method of claim 47, comprising conveying the light from the light source to the light projector by optical fibers extending between the canopy and a pole of the MRI magnet assembly, to the light projector.

49. The method of claim 44, further comprising flexing the light projector to aim illumination from the light projector onto a canopy covering a pole of the MRI magnet assembly, to provide diffuse illumination in the imaging volume.

50. The method of claim 44, wherein the magnet assembly defines an imaging volume, the method comprising:
    flexing a light projector connected to the magnet assembly in a recessed portion of the magnet assembly positioned within the imaging volume.

* * * * *